United States Patent [19]

Monroe et al.

[11] Patent Number: 5,092,843
[45] Date of Patent: Mar. 3, 1992

[54] DISPERSION MULTICHAMBER AUTO-INJECTOR

[75] Inventors: O. Napoleon Monroe, Bethesda, Md.; N. Lawrence Dalling, Cross Junction, Va.; Clarence M. Mesa, Rockville, Md.

[73] Assignee: Survival Technology, Inc., Bethesda, Md.

[21] Appl. No.: 507,756

[22] Filed: Apr. 12, 1990

[51] Int. Cl.⁵ .............................................. A61M 5/20
[52] U.S. Cl. .................... 604/138; 604/137; 604/195; 604/191
[58] Field of Search .................. 604/90, 91, 130, 134, 604/135, 136, 138, 191, 187, 90, 91, 218, 195, 196

[56] References Cited

U.S. PATENT DOCUMENTS

| | | | |
|---|---|---|---|
| 2,832,339 | 4/1958 | Sarnoff et al. | 604/138 |
| 3,396,726 | 8/1968 | Sarnoff | 604/138 |
| 3,712,301 | 1/1973 | Sarnoff | 604/136 |
| 3,882,863 | 5/1975 | Sarnoff et al. | 604/136 |
| 4,031,893 | 6/1977 | Kaplan et al. | 604/136 |
| 4,226,235 | 10/1980 | Sarnoff et al. | 604/136 |
| 4,329,988 | 5/1982 | Sarnoff et al. | 604/137 |
| 4,394,863 | 7/1983 | Bartner | 604/90 |
| 4,529,403 | 7/1985 | Kamstra | 604/136 |
| 4,578,064 | 3/1986 | Sarnoff et al. | 604/191 |
| 4,820,286 | 4/1989 | Vanderwal | 604/90 |
| 4,822,340 | 4/1989 | Kamstra | 604/191 |
| 4,929,230 | 5/1990 | Pfleger | 604/191 |

OTHER PUBLICATIONS

LTC Willis H. Jacob et al., "Drug Delivery Systems for Chemical Defense", Army RD&A Bulletin, Jan.-Feb. 1990, pp. 14-16.
Karl E. Friedl et al., "Atropine Absorption after Intramuscular Administration with 2-Pralidoxime Chloride by Two Automatic Injector Devices", Journal of Pharmaceutical Sciences, vol. 78, No. 9, Sep. 1989, pp. 728-731.

Primary Examiner—Gene Mancene
Assistant Examiner—Michael Lynch
Attorney, Agent, or Firm—Cushman, Darby & Cushman

[57] ABSTRACT

A medicament container assembly for an autoinjector having a power assembly actuatable to cause a power stroke in cooperating relation with said medicament container assembly. The medicament container assembly comprises a container having a forward end, a hypodermic needle having a sharpened end, and first and second liquid medicaments. A pair of pistons and a closure assembly are provided for (1) sealingly confining the first liquid medicament and the needle in mutually communicating relation in a forward storage position within the container, (2) sealingly confining the second liquid medicament within the container in a separate rearward storage position, and (3) enabling the power stroke to cause (1) an initial movement of the needle into the injection site during which the sharpened end of the needle moves from a position of entry into the skin to a full depth position, (2) a progressive movement of the first medicament outwardly of the sharpened end of the needle as the sharpened end of the needle moves from the position of entry into the skin into the full depth position so as to inject a predetermined dosage of the first liquid medicament within the injection site in a first pattern surrounding the path of movement of the sharpened end of the needle, and (3) a progressive movement of the second medicament outwardly of the sharpened end of the needle generally after the sharpened end of the needle has reached the full depth position thereof to inject a predetermined dosage of the second liquid medicament within the injection site in a second pattern extending from the sharpened end of the needle.

22 Claims, 2 Drawing Sheets

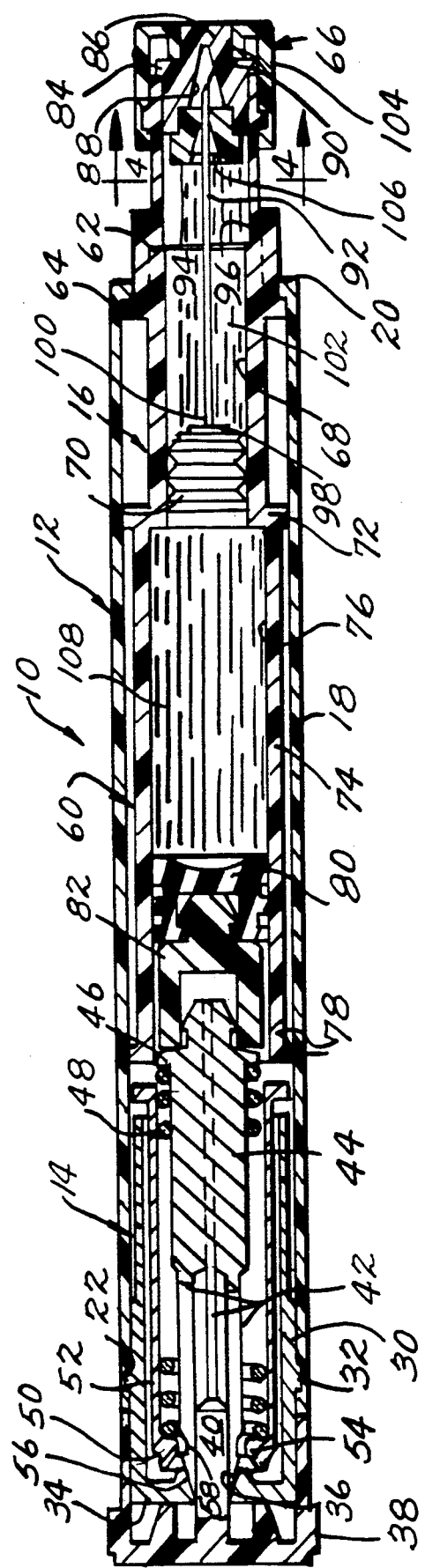
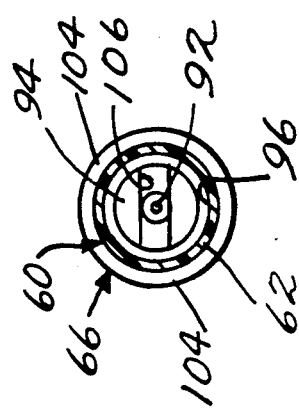
Fig. 1.
Fig. 4.

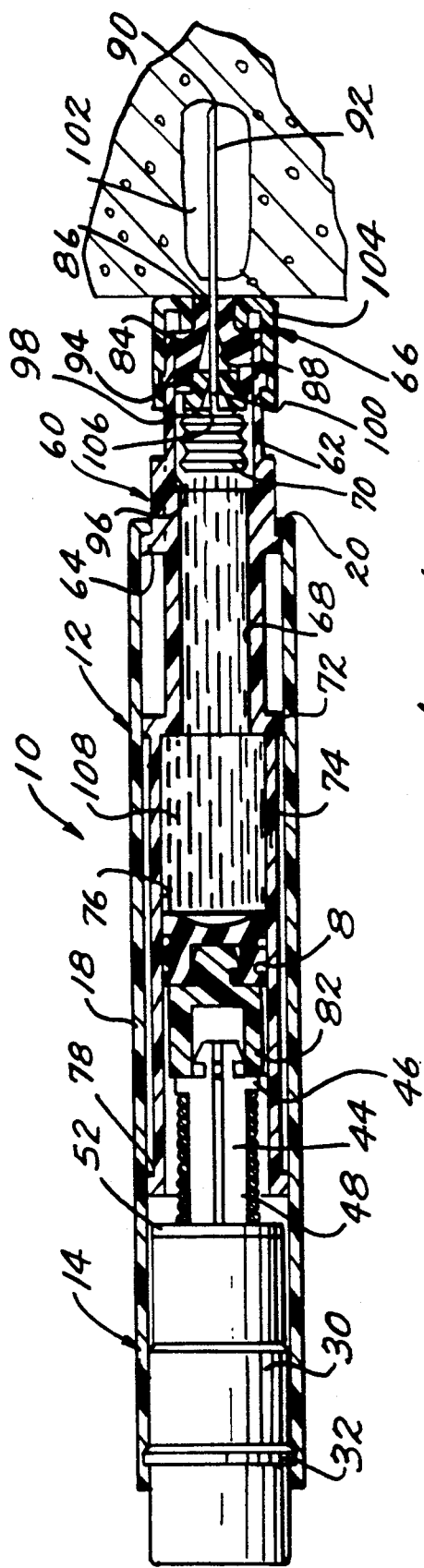
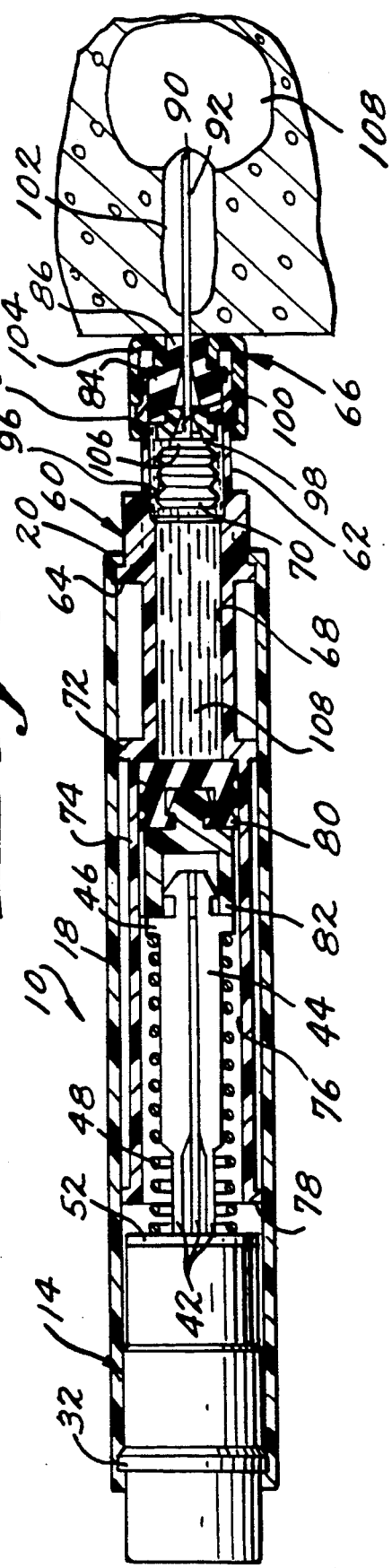

DISPERSION MULTICHAMBER AUTO-INJECTOR

This invention relates to the administration of medicaments and particularly to the administration of medicaments under emergency conditions.

A well-known example of an emergency condition requiring the delivery of medicaments is the need to provide an antidote for nerve agents when an emergency situation of this kind is presented. A recent article in the Army RD&A Bulletin dated January-February 1990 entitled "Drug Delivery Systems for Chemical Defense" by LTC Willis H. Jacob and CPT Karl E. Friedl contains a recitation of the history of drug delivery systems for nerve gas antidotes and a fine summary of the present state of the art. Briefly, for the last several years, the indicated medicament is a combination of atropine and 2-pralidoxime chloride (PAMCL). As stated in the publication, the initial drug delivery system for delivering atropine and PAMCL was referred to as the MARK I device, a disclosure of which is contained in U.S. Pat. No. 4,329,988. As shown therein, the MARK I device consisted essentially of an auto-injector of the type disclosed in U.S. Pat. No. 2,832,339 (see also U.S. Pat. No. 3,396,726) containing a dosage of atropine, an auto-injector of the type disclosed in U.S. Pat. No. 4,031,893 (see also U.S. Pat. No. 3,882,863) containing a dosage of PAMCL therein, and a holder for the two automatic injectors receiving the safety caps thereof to facilitate sequential use of the two auto-injectors. As stated in the aforesaid article, studies have shown that when atropine and PAMCL were combined in a single syringe, the high concentration of PAMCL slowed the atropine absorption. Consequently, the use of two separate injectors was considered to obviate the results of this study. (See also the article entitled "Atropine Absorption after Intramuscular Administration with 2-Pralidoxime Chloride by Two Automatic Injector Devices" by Karl E. Friedl et al., in the Journal of Pharmaceutical Sciences, Vol. 78, No. 9, September 1989, pp. 728-731).

Since that time, there have been two proposals which would simplify the procedures for effecting the injection of the two components, the first of these devices was designated the MARK II. One embodiment of the MARK II device is illustrated in FIG. 7 of U.S. Pat. No. 4,226,235. Another embodiment is disclosed in U.S. Pat. No. 4,578,064. In both of these embodiments, a single housing is provided for containing the two auto-injectors of the MARK I device, the arrangement being such that a single actuation would serve to actuate both auto-injectors substantially simultaneously so that the atropine and PAMCL is delivered through two parallel needles.

The second device was much simpler in construction and embodied only a single needle is disclosed in U.S. Pat. No. 4,394,863 (see also U.S. Pat. No. 4,529,403). In these latter devices, the atropine and PAMCL were stored within tandem chambers in a single medicament cartridge assembly so as to be sequentially delivered through a single needle. In all of the proposed tandem chamber auto-injectors, the operation was such that the needle was initially inserted into the muscle tissue of the user into a full depth position after which the medicaments are sequentially moved through the needle while the needle is in its full depth position. Thus, while the medicaments are stored separately and injected sequentially, the injection is at the same site and, consequently, the studies as to combination of the two drugs slowing the absorption rate of the atropine may be presented after the injection has taken place. In all of the other devices, there existed a differentiation between the injection sites of the two drugs. In the case of the MARK I, even if the two injectors were injected essentially in the same injection site, the delivery of the two components even in the same site were different because, with the atropine injector, the atropine was injected during the movement of the needle into the muscle tissue rather than after the movement of the needle into its full depth position. With the MARK II, these two patterns of delivery were utilized but in spaced injection sites by virtue of the provision of the two needles disposed in fixed parallel relation with respect to one another.

An object of the present invention is to provide an automatic injector which has all of the advantages of all of the above-identified devices without the disadvantages thereof. In accordance with the principles of the present invention, this objective is obtained by providing an auto-injector which includes a medicament cartridge assembly, a stressed spring assembly, and means mounting said assemblies together in cooperating relation so as to provide an exterior housing having a needle extending end. The medicament cartridge assembly includes a container having one end disposed adjacent to the needle extending end of the housing. The first piston is mounted in a storage position within the container in spaced relation with the one end thereof for movement therein from the storage position thereof through an operative stroke in a direction toward the one end thereof. A hollow hypodermic needle having a sharpened end and an opposite inlet end portion is disposed within the container in a storage position to be moved therefrom by and with the first piston during the operative stroke thereof. A closure assembly enclosing the sharpened end of the needle and the one end of the container is disposed in a position to be penetrated by the sharpened end of the needle when the needle is moved with the first piston. A first liquid medicament, as, for example, atropine, is disposed within the container in a storage position between the first piston and the closure assembly. A second piston is mounted in a storage position within the container in spaced relation with respect to the storage position of the first piston for movement from the storage position thereof through an operative stroke in a direction toward the closure assembly. A second liquid medicament, as, for example, PAMCL, is disposed in the container in a storage position in motion transmitting relation between the second piston and the first piston in sealed relation with respect to the first liquid medicament. The operative relation of the first liquid medicament and the needle between the first piston and the closure assembly when in the storage positions thereof within the container being such that when the first piston is moved through the operative stroke thereof, the needle is moved by the first piston so that (1) during an initial portion of the movement of the needle with the first piston, the sharpened end of the needle penetrates through the closure assembly beyond the needle extending end of the housing and into the skin of a user without significant passage of the first liquid medicament from the sharpened end of the needle and (2) during the remaining portion of the movement of the needle with the first piston, the first liquid medicament is moved into the inlet end of the needle and out of the sharpened end thereof and into the tissue of the user as the sharpened end moves inwardly of the skin into a full depth position. The stressed spring assembly includes a spring, a releasable assembly for retaining the spring in a stressed storage position, and a releasing assembly operable in response to a predetermined manual actuating procedure to release the releasable assembly so that the spring moves the second piston through the operative stroke thereof during an initial portion of which the first piston is moved through the operative stroke thereof. The medicament cartridge assembly also includes a bypass arrangement operable in response to the movement of the first piston through a final portion of the operative stroke thereof to allow a subsequent remaining portion of the operative stroke of the second piston to move the second liquid medicament beyond the first piston into the inlet end portion of the needle and out of the sharpened end thereof generally after the sharpened end has reached its full depth position.

In its broadest aspects, the invention constitutes a medicament container assembly for an auto-injector having a power assembly actuatable to cause an elongated element thereof to move through a power stroke in cooperating relation with said medicament container assembly. The medicament container assembly of the invention comprises a container having a forward end, a hypodermic needle having a sharpened end, first and second liquid medicaments and structure for (1) sealingly confining said first liquid medicament and the needle in mutually communicating relation in a forward storage position within the container, (2) sealingly confining the second liquid medicament within the container in a rearward storage position separate from the first liquid medicament and the needle and (3) enabling a movement of the elongated element of the power assembly through a power stroke in cooperating relation with the medicament container assembly while the forward end of the container is held in cooperating relation with an injection site of a user to cause (1) an initial movement of the needle into the injection site during which the sharpened end of the needle moves from a position of entry into the skin to a full depth position, (2) a progressive movement of the first medicament outwardly of the sharpened end of the needle as the sharpened end of the needle moves from the position of entry into the skin into the full depth position so as to inject a predetermined dosage of the first liquid medicament within the injection site in a first pattern generally surrounding the path of movement of the sharpened end of the needle from the position of entry to the full depth position and (3) a progressive movement of the second medicament outwardly of the sharpened end of the needle generally after the sharpened end of the needle has reached the full depth position thereof to inject a predetermined dosage of the second liquid medicament within the injection site in a second pattern generally extending from the sharpened end of the needle in surrounding relation to the full depth position of the sharpened end of the needle.

It can thus be seen that the cost effectiveness and single needle operational advantages of the more recently proposed tandem dosage auto-injectors are retained while eliminating the single injection pattern disadvantages thereof and instead substantially retaining the advantages of the MARK I and II devices as to separate injection patterns in the injection site.

Another object of the present invention is the provision of an auto-injector with an improved medicament cartridge assembly which is simple in construction, effective in operation and economical to manufacture and maintain.

These and other objects of the present invention will become more apparent during the course of the following detailed description and appended claims.

The invention may best be understood with reference to the accompanying drawings wherein an illustrative embodiment is shown.

IN THE DRAWINGS

FIG. 1 is a longitudinal sectional view of an auto-injector embodying the principles of the present invention, showing the same in its normal storage position;

FIG. 2 is a view similar to FIG. 1, showing the position of the parts just after the completion of the injection of the first liquid medicament during operation;

FIG. 3 is a view similar to FIG. 1, showing the position of the parts after the injection of the second liquid medicament: and FIG. 4 is a sectional view taken along the line 4—4 of FIG. 1.

Referring now more particularly to the drawings, there is shown therein an automatic injector, generally indicated at 10, which embodies the principles of the present invention. The injector consists essentially of two basic assemblies held together in cooperating relation in a storage position by a housing member, generally indicated at 12. The first basic assembly is a power pack or stressed spring assembly, generally indicated at 14, secured to the rearward end of the housing member 12 and operable in response to a predetermined manual actuating procedure to be released so as to operate the second assembly, which is a medicament injection cartridge assembly, generally indicated at 16, embodying the principles of the present invention. While the housing member 12 and stressed spring assembly 14 can assume any known configuration, the preferred embodiment as shown is constructed in accordance with the teachings contained in U.S. Pat. Nos. 3,712,301 and 3,882,863, which disclosures are hereby incorporated by reference into the present specification.

As best shown in FIGS. 1 and 2, the housing member 12 includes an outer tubular member 18 having a radially inwardly turned flange 20 on the forward end thereof and an interior annular groove 22 in the rearward end thereof.

The stressed spring assembly 14 as preassembled includes an outer tubular member 30 having an annular ridge 32 formed on the exterior periphery thereof adjacent the rearward end portion which serves to engage within the annular groove 22 of the outer tubular member 18 when the injector is assembled in operative position, as shown in FIG. 1. The outer tubular member 30 includes a rearward end wall 34 having a central opening therein defined by a frustoconical surface 36 which diverges inwardly. The stressed spring assembly includes a safety cap 38 which detachably fits over the portion of the outer member 30 extending rearwardly from the outer tubular member 18. The safety cap 38 includes a central inwardly extending safety pin 40 which in its normal preassembly position extends through and inwardly of the frustoconical surface 36.

The safety pin 40 is adapted to cooperate with a plurality of spring fingers 42 extending from the rear end of an elongated collet member 44 having extensions 46 extending radially outwardly from the forward end thereof. The rearward surface of the extensions 46 is adapted to engage one end of a stressed coil spring 48, the other end of which engages an apertured rear wall 50 of a tubular member 52 slidably mounted within the tubular member 30. The apertured end wall 50 has formed therein an apertured catch plate or disc 54. The central opening of the catch plate 54 is of a size to engage inclined surfaces 56 formed on the outer rearward portions of the spring fingers 42 so as to deflect the fingers radially inwardly as the rearward ends of the fingers pass rearwardly therethrough. Each spring finger 42 has formed therein an exterior catch receiving notch 58 which is adapted to receive the catch plate 54 when the spring fingers 42 have been moved rearwardly through the catch plate into the normal spring stressed preassembly position, as shown in FIG. 1. In this regard, it will be noted that safety pin 40 engages within the inner surfaces of the spring fingers 42 and hence prevents their radially inward movement so that the tubular member 30 and 52, collet member 44 and safety cap 38 can be preassembled and mounted in operative position within the outer tubular member 18 as a unit. In the operative position, the members 30 and 52 of the power pack assembly 14 may be regarded as part of a housing which includes the housing member 12.

The medicament cartridge assembly 16, which is constructed in accordance with the principles of the present invention, includes a medicament container, generally indicated at 60, which, as shown, is preferably molded of a suitable plastic material, as, for example, polypropylene, Teflon ®, or other suitable materials. The container 60 includes a forward end portion 62, forming a part of the housing, which is defined rearwardly by a radially outwardly extending flange 64. The forward end portion 62 of the container 60 is opened and closed by a closure assembly, generally indicated at 66. The container 60 extends rearwardly from the forward end portion 62 thereof and includes a first inner cylindrical surface 68 having a first diameter within which is slidably mounted a first piston 70. The first piston 70 is preferably formed of a resilient material so as to have its exterior periphery in slidable sealing engagement with the rearward end of the first cylindrical surface 68 when the components of the medicament cartridge assembly 16 are in their storage position.

As shown, the container 60 includes an intermediate annular wall 72 which defines an annular shoulder extending radially outwardly from the rearward end of the cylindrical surface 68. The container 60 includes a rearward end portion 74 defining a second interior cylindrical surface 76 extending rearwardly from the shoulder 72 which has a diameter size greater than the diameter size of the first cylindrical surface 68. The rearward end portion 74 of the container 60 terminates in a rearward radially outwardly extending flange 78. As shown, the container 60 is retained by the housing member 18 in a storage position within the housing member 18 with the exterior peripheries of the rearward flange 78 and the intermediate wall 72 in engagement with the interior of the housing member 18 and the annular flange 64 engaged with the inwardly extending flange 20 of the housing member 18.

A second piston 80 is mounted within the rear end portion 74 of the container 60 in forwardly spaced relation from the rearward flange 78 thereof. The second piston 80 is preferably made of a resilient material so that its exterior periphery is disposed in slidable sealed relation with respect to the interior cylindrical surface 76 provided by the container 60. As shown, a spacer 82 is interposed between the second piston 80 and the forward end of the collet member 44 in accordance with the teachings of U.S. Pat. No. 4,031,893, the disclosure of which is hereby incorporated by reference into the present specification.

The forward closure assembly 66 includes an inner closure member 84 defining a rearward annular portion which is engaged within the forward open end of the forward end portion 62 of the container 60. The inner closure member 84 includes a forwardly extending central wall portion which closes the forward end of the container 60. The inner closure member 84 is preferably made of a resilient material and its rearward annular portion defines a central recess 88 within which the forward sharpened end 90 of a hypodermic needle 92 is disposed. The closure assembly 66 includes a needle guide 94 which is frictionally engaged and held and slidably receives the hypodermic needle 92 therethrough in a storage position spaced slightly rearwardly of the sharpened end 90 of the needle. As shown, the interior cylindrical surface 68 is provided with bypass means at its forward end portion in the form of a cylindrical bypass surface 96 of a diameter size slightly greater than the diameter size of the cylindrical surface 68.

It will be noted that the forward end portion of the hypodermic needle 92 terminates in an enlarged head 98. A transverse opening 100 defining an inlet for the hypodermic needle 92 is formed therein in a position forwardly adjacent the head 98. The first cylindrical surface 68 and the bypass surface 96 in the forward portion thereof define with the closure assembly 66 and the first piston 70, a medicament chamber within which the hypodermic needle 92 is mounted and within which a first liquid medicament 102 is contained in communication with the needle 92. Preferably, the amount of liquid medicament 102 within the first liquid medicament chamber has a volume less than the volume of the chamber so as to enable the sharpened end 90 of the needle 92 to be moved forwardly a distance sufficient to penetrate the central closure wall portion and preferably slightly into the injection site without the passage of liquid medicament therethrough. This arrangement is in accordance with the teachings contained in U.S. Pat. No. 3,396,726, the disclosure of which is hereby incorporated by reference into the present specification. It will be understood that other equivalent arrangements for accomplishing this purpose can be provided.

As shown, the closure assembly 66 also includes an outer closure securing member 104 having a forward surface which aligns with the forward surface of the central wall portion 86 of the inner closure member 84 to constitute a skin engaging surface of the injector 10 through which the needle 92 extends. As shown, the securing member 104 includes an outer annular wall having an annular groove formed interiorly thereof which is adapted to snap over an annular ridge on the exterior of the forward end portion 62 of the container 60. The securing member 104 also includes an inner annular wall which engages the inner closure member 84 to retain the same in closing relation to the open end of the container 60.

As best shown in FIG. 4, a rearward end portion of the needle guide 94 has a diametrically extending groove 106 formed therein of a width less than the diameter of the needle head 98. The needle guide 94 is thus configured so as to receive the head 98 of the hypodermic needle 92 after the same has been moved through its operative stroke and to provide opposed paths inwardly of the ends of the groove 106 during operation for the flow of a piston-bypassing second liquid medicament into the adjacent inlet opening 100 of the needle 92. The second medicament 108 is mounted within a second medicament chamber defined by the second cylindrical surface 76 between the first piston 70 and second piston 80. Preferably, the second liquid medicament 108 is disposed within the chamber in motion transmitting relation within the chamber between the two pistons.

In the embodiment shown, the first liquid medicament 102 is atropine and the second liquid medicament 108 is PAMCL. While these two medicaments constitute a preferred embodiment, it will be understood that other liquid medicaments may be accommodated as well, if desired. Indeed, it is within the contemplation of the invention that the two medicaments can be the same medicament when it is desired to achieve the improved medicament distribution pattern of the present invention with the same medicament. In general, it can be stated, however, that the separate containment of the two medicaments lends itself to the accommodation of two different medicaments which are not compatible in storage with the metal of the needle.

OPERATION

FIG. 1 illustrates the assembled storage position of the automatic injector 10 and it will be noted that the stressed spring assembly 14 includes the assembled safety cap 38 which serves to prevent the spring fingers from moving radially inward to release the stressed spring. The cartridge assembly 16 is mounted forwardly within the housing assembly 12 in cooperating relation with the stressed spring assembly 14. As previously indicated, the forward and rearward liquid medicaments are sealed within the container 60 in the manner previously indicated. When it is desired to inject the medicaments, the safety cap 38 is initially removed, thus displacing the safety pin 40 from its storage position within the spring fingers and hence permitting the same to move radially inwardly.

The actuation procedure consists in the user manually gripping the exterior periphery of the outer tubular member 18 and then moving the injector forwardly into contact with the muscle tissue to be injected, as for example, a thigh. When the forward end of the member 104 engages the exterior of the thigh, continued forward movement exerted on the exterior periphery of the outer member results in a relative longitudinal movement between rear end walls 50 and 34, causing the frustoconical surface 36 to engage the spring finger surfaces 56 and thus move the same radially inwardly by a camming action so as to disengage the notch 58 from the catch plate, thus releasing the stressed spring 48.

As the stressed spring 48 is released, the forward end of the collet member 44 starts to move forward in motion-transmitting relation with respect to the spacer 82, the second piston 80, the second liquid medicament 108, and first piston 70. Since there is a pocket of air in the first medicament chamber, the piston 70 moves forward carrying with it the hypodermic needle 92. During the initial portion of the movement of the needle with the piston 70, the sharpened end 90 of the hypodermic needle 92 moves through the closure wall portion 86 and into the skin at the injection site. During this movement, the air within the chamber is compressed. Thereafter, as the first piston 70 continues to move forward carrying with it the needle 92, the first liquid medicament 102 is moved out of the chamber through the needle 92 and into the tissue at the injection site. This concomitant movement of the piston 70, the needle 92 and the liquid medicament 102 continues until the resilient periphery of the piston 70 passes into the bypass cylindrical surface 96 throughout the axial extent thereof, as shown in FIG. 2. At this point, the needle 92 has been moved virtually into its full depth position. However, the spacing of the periphery of the piston 70 with the bypass surface 96 creates an annular passageway which enables the second liquid medicament 108 which is moving forwardly with the forward movement of the second piston 80 and first piston 70 to move past the first piston 70 along the annular passageway and then into the groove 106 and the rearward recess of the needle guide 94 to enter the needle opening 100.

As shown in FIG. 2, substantially the entire first liquid medicament 102 is injected into the injection site as the sharpened end 90 of the needle 92 moves inwardly within the tissue at the injection site so as to establish an injection pattern which is schematically illustrated in FIG. 2. As the stressed spring 48 continues to move the collet member 44 forwardly together with the spacer 82 and second piston 80, the second liquid medicament 108 which is now in communication with the needle past the first piston 70, as aforesaid, can be discharged through the needle at the injection site forwardly of the sharpened end 90 of the needle retained in its full depth position. This movement of the second liquid medicament 108 outwardly of the needle 92 continues until the second piston 80 reaches the shoulder 72 and the end of its stroke at which time a proper dosage of the second liquid medicament 108 has been injected into the muscle tissue in the second pattern as schematically illustrated in FIG. 3.

As can be clearly seen from FIG. 3, the injection pattern of the atropine 102 is different from the injection pattern of the PAMCL 108 thus maintaining this desirable characteristic even though there is utilized a single needle 92 through which both medicaments are injected.

It will be noted that there is a volume of liquid medicament 108 left between the first and second pistons 80 and 70 which is simply retained in the auto-injector. If desired, the forward piston 70 can be extended rearwardly at a lesser diameter into the second chamber to substantially fill the space therein which is taken up by the excess liquid medicament.

It will be understood that the enlarged bypass cylindrical surface 96 is merely illustrative of one preferred means for effecting the bypass of the second liquid medicament 108 past the first piston 70. Other bypass arrangements around the exterior periphery of the piston 70 can be utilized as, for example, annularly spaced ribs on the surface 68 as well as bypass arrangements which provide for the bypass of the liquid through the piston 70 so that it can move past the piston 70.

The two medicament chambers are disclosed as having different diameter dimensions in order to accommodate the larger volume of the dosage of PAMCL 108 as compared with the smaller dosage of atropine 102. It will be understood that, when the principles of the present invention are applied to other plural medicaments in which the dosages are more nearly equal, there need not be any difference in the diameter dimension of the two chambers, in which case the second piston 80 ends up in abutting relation with the first piston 70 and a differential volume need not be accommodated.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An auto-injector comprising a medicament cartridge assembly, a stressed spring assembly, and means mounting said assemblies together in cooperating relation so as to provide an exterior housing having a needle extending end, said medicament cartridge assembly including a container having one end disposed adjacent the needle extending end of said housing, first piston means mounted in a storage position within said container in spaced relation with the one end thereof for movement therein from the storage position thereof through an operative stroke in a direction toward the one end thereof, a hollow hypodermic needle having a sharpened end and an opposite inlet end portion disposed within said container in a storage position to be moved therefrom by and with said first piston means during the operative stroke thereof, closure means enclosing the sharpened end of said needle and the one end of said container disposed in a position to be penetrated by the sharpened end of said needle when said needle is moved with said first piston means, a first liquid medicament within said container in a storage position between said first piston means and said closure means, second piston means mounted in a storage position within said container in spaced relation with respect to the storage position of said first piston means for movement from the storage position thereof through an operative stroke in a direction toward said closure means, a second liquid medicament in said container disposed in a storage position in motion transmitting relation between said second piston means and said first piston means in sealed relation with respect to said first liquid medicament, the operative relation of said first liquid medicament and said needle between said first piston means and said closure means when in said storage positions within said container being such that when said first piston means is moved through the operative stroke thereof said needle is moved by said first piston means so that (1) during an initial portion of the movement of said needle with said first piston means the sharpened end of said needle penetrates through said closure means beyond the needle extending end of said housing and into the skin of a user without significant passage of said first liquid medicament from the sharpened end of the needle and (2) during the remaining portion of the movement of the needle with the first piston means, the first liquid medicament is moved into the inlet end of the needle and out of the sharpened end thereof and into the tissue of the user as the sharpened end moves inwardly of the skin into a full depth position, said stressed spring assembly including spring means, releasable means for retaining said spring means in a stressed storage position, and releasing means operable in response to a predetermined manual actuating procedure to release said releasable means so that said spring means moves said second piston means through the operative stroke thereof during an initial portion of which said first piston means is moved through the operative stroke thereof, said medicament cartridge assembly including bypass means operable in response to the movement of said first piston means through a final portion of the operative stroke thereof to allow a subsequent remaining portion of the operative stroke of said second piston means to move said second liquid medicament beyond said first piston means through said needle and out of the sharpened end thereof generally after the sharpened end has reached its full depth position.

2. An auto-injector as defined in claim 1 wherein said first piston means comprises a first piston having a resilient periphery, said container including a first interior generally cylindrical surface disposed in sealing engagement with the resilient periphery of said first piston and extending therefrom toward said closure means so as to be slidably sealingly engaged by the resilient periphery of said first piston during the operative stroke thereof.

3. An auto-injector as defined in claim 2 wherein said bypass means is located at an end portion of said first interior cylindrical surface adjacent the closure means and is operable to allow the second liquid medicament to move beyond said first piston exteriorly of the resilient periphery thereof.

4. An auto-injector as defined in claim 3 wherein said bypass means includes a cylindrical bypass surface extending from said one end of said container beyond said closure means a distance slightly greater than the longitudinal extent of the resilient periphery of said first piston and terminating at the forward end of said first interior cylindrical surface so as to provide an annular passageway around the resilient periphery of said first piston when said first piston moves in longitudinally coextensive relation thereto.

5. An auto-injector as defined in claim 4 wherein said inlet end portion of said needle includes a motion transmitting head fixed on the extremity of said needle and an inlet opening communicating transversely with the hollow interior of said needle adjacent said head.

6. An auto-injector as defined in claim 5 wherein said closure member includes an annular portion extending within the one end of said container and defining a recess within which the sharpened end of said needle is disposed in the storage position thereof and a needle guide fixed within said annular portion having an opening through which said needle extends, said needle guide being shaped to (1) engage said needle head when the sharpened end of said needle reaches its full depth position and (2) maintain a liquid flow path into the inlet opening of said needle adjacent to said head.

7. An auto-injector as defined in claim 6 wherein said second piston means comprises a second piston having a resilient periphery of a diameter size greater than the diameter size of the resilient periphery of said first piston, said container including a second interior generally cylindrical surface disposed in sealing engagement with the resilient periphery of said second piston and extending therefrom toward the first interior cylindrical surface so as to be slidably sealingly engaged by the resilient periphery of said second piston during the operative stroke thereof, said container providing a shoulder between said first and second interior cylindrical surfaces defining the end of the operative stroke of said second piston.

8. An auto-injector as defined in claim 7 wherein said releasing means includes an outer tubular releasing member, said assembly mounting means including a tubular member providing a substantial part of said housing, said housing providing tubular member being fixedly connected with said tubular releasing member and mounted for movement therewith in surrounding telescopic relation with respect to a substantial portion of said container, said releasing means further including a safety cap structure having a skirt portion normally positioned over said tubular releasing member, said predetermined actuating procedure including removing said safety cap structure manually from its normal position and moving the needle extending end of said housing toward the injection site by manually gripping said housing providing tubular member until a relative longitudinal movement of said tubular members with respect to said container in a direction toward the injection site takes place as a result of the injection site stopping the movement of the container, said releasable means being released in response to said relative longitudinal movement.

9. An auto-injector as defined in claim 8 wherein said releasable means comprises an inner tubular member disposed within said outer tubular releasing member and an elongated member having spaced fingers on one end thereof movable laterally from a locking position inwardly into a releasing position, said inner tubular member including an end wall having a central aperture therein, said fingers having locking surfaces spaced from free ends thereof for engaging locking surfaces on the end wall of said inner tubular member and releasing surfaces between said locking surfaces and the free ends thereof, said spring means comprising a helical coil spring surrounding said elongated member, said elongated member having means on the end thereof opposite from said fingers for engaging one end of said coil spring, said elongated member in a storage position releasably retaining said coil spring in a compressively stressed condition with, free end portions of said fingers extending through the central aperture of the end wall of said inner tubular member and with the locking surfaces thereof engaging the locking surfaces on the end wall of said inner tubular member, said safety cap structure including a central safety rod disposed between said fingers when said safety cap structure is in its normal position so as to prevent lateral movement of said fingers and hence disengagement of said locking surfaces, said outer tubular releasing member including an end wall having releasing surfaces positioned to engage the releasing surfaces of said fingers during the relative longitudinal movement of said tubular members with respect to said container to cause said fingers to move laterally inwardly when said safety rod is removed and disengage said locking surfaces to release said spring means to thereby move said elongated member through an operative stroke during which said second piston is moved through the operative stroke thereof.

10. An auto-injector as defined in claim 9 wherein the operative relation of said first liquid medicament and said needle between said first piston means and said closure means in the storage positions thereof within said container is one in which the volume of first liquid medicament and needle is less than the volume within said container between said first piston means and said closure means so as to leave a volume of gas therein which is compressed during the initial portion of the movement of the needle as aforesaid.

11. An auto-injector as defined in claim 10 wherein said first liquid medicament is atropine.

12. An auto-injector as defined in claim 11 wherein said second liquid medicament is 2-pralidoxime chloride.

13. An auto-injector as defined in claim 2 wherein said second piston means comprises a second piston having a resilient periphery of a diameter size greater than the diameter size of the resilient periphery of said first piston, said container including a second interior generally cylindrical surface disposed in sealing engagement with the resilient periphery of said second piston and extending therefrom toward the first interior cylindrical surface so as to be slidably sealingly engaged by the resilient periphery of said second piston during the operative stroke thereof, said container providing a shoulder between said first and second interior cylindrical surfaces defining the end of the operative stroke of said second piston.

14. An auto-injector as defined in claim 1 wherein said inlet end portion of said needle includes a motion transmitting head fixed on the extremity of said needle and an inlet opening communicating transversely with the hollow interior of said needle adjacent said head.

15. An auto-injector as defined in claim 14 wherein said closure member includes an annular portion extending within the one end of said container and defining a recess within which the sharpened end of said needle is disposed in the storage position thereof and a needle guide fixed within said annular portion having an opening through which said needle extends, said needle guide being shaped to (1) engage said needle head when the sharpened end of said needle reaches its full depth position and (2) maintain a liquid flow path into the inlet opening of said needle adjacent to said head.

16. An auto-injector as defined in claim 1 wherein said releasing means includes an outer tubular releasing member, said assembly mounting means including a tubular member providing a substantial part of said housing, said housing providing tubular member being fixedly connected with said tubular releasing member and mounted for movement therewith in surrounding telescopic relation with respect to a substantial portion of said container, said releasing means further including a safety cap structure having a skirt portion normally positioned over said tubular releasing member, said predetermined actuating procedure including removing said safety cap structure manually from its normal position and moving the needle extending end of said housing toward the injection site by manually gripping said housing providing tubular member until a relative longitudinal movement of said tubular members with respect to said container in a direction toward the injection site takes place as a result of the injection site stopping the movement of the container, said releasable means being released in response to said relative longitudinal movement.

17. An auto-injector as defined in claim 16 wherein said releasable means comprises an inner tubular member disposed within said outer tubular releasing member and an elongated member having spaced fingers on one end thereof movable laterally from a locking position inwardly into a releasing position, said inner tubular member including an end wall having a central aperture therein, said fingers having locking surfaces spaced from free ends thereof for engaging locking surfaces on the end wall of said inner tubular member and releasing surfaces between said locking surfaces and the free ends thereof, said spring means comprising a helical coil spring surrounding said elongated member, said elongated member having means on the end thereof opposite from said fingers for engaging one end of said coil spring, said elongated member in a storage position releasably retaining said coil spring in a compressively stressed condition with free end portions of said fingers extending through the central aperture of the end wall of said inner tubular member and with the locking surfaces thereof engaging the locking surfaces on the end wall of said inner tubular member, said safety cap structure including a central safety rod disposed between said fingers when said safety cap structure is in its normal position so as to prevent lateral movement of said fingers and hence disengagement of said locking surfaces, said outer tubular releasing member including an end wall having releasing surfaces positioned to engage the releasing surfaces of said fingers during the relative longitudinal movement of said tubular members with respect to said container to cause said fingers to move laterally inwardly when said safety rod is removed and disengage said locking surfaces to release said spring means to thereby move said elongated member through an operative stroke during which said second piston means is moved through the operative stroke thereof.

18. An auto-injector as defined in claim 1 wherein the operative relation of said first liquid medicament and said needle between said first piston means and said closure means in the storage positions thereof within said container is one in which the volume of first liquid medicament and needle is less than the volume within said container between said first piston means and said closure means so as to leave a volume of gas therein which is compressed during the initial portion of the movement of the needle as aforesaid.

19. An auto-injector as defined in claim 1 wherein said first liquid medicament is atropine.

20. An auto-injector as defined in claim 19 wherein said second liquid medicament is 2-pralidoxime chloride.

21. A medicament container assembly for an auto-injector having a power assembly actuatable to cause an elongated element thereof to move through a power stroke in cooperating relation with said medicament container assembly, said medicament container assembly comprising a container having a forward end,
a hypodermic needle having a sharpened end,
first and second liquid medicaments,
means for (1) sealingly confining said first liquid medicament and said needle in mutually communicating relation in a forward storage position within said container, (2) sealingly confining said second liquid medicament within said container in a rearward storage position separate from said first liquid medicament and said needle and (3) enabling a movement of the elongated element of the power assembly through a power stroke in cooperating relation with said medicament container assembly while the forward end of said container is held in cooperating relation with an injection site of a user to cause (1) an initial movement of said needle into the injection site during which the sharpened end of the needle moves from a position of entry into the skin to a full depth position, (2) a progressive movement of said first medicament outwardly of the sharpened end of said needle as the sharpened end of the needle moves from the position of entry into the skin into said full depth position so as to inject a predetermined dosage of said first liquid medicament within the injection site in a first pattern generally surrounding the path of movement of the sharpened end of said needle from the position of entry to the full depth position and (3) a progressive movement of said second medicament outwardly of the sharpened end of said needle generally after the sharpened end of the needle has reached the full depth position thereof to inject a predetermined dosage of said second liquid medicament within the injection site in a second pattern generally extending from the sharpened end of the needle in surrounding relation to the full depth position of the sharpened end of the needle.

22. A medicament container assembly as defined in claim 21 wherein the first medicament is atropine and the second medicament is 2-pralidoxime chloride, the volume of the predetermined dosage of said 2-pralidoxime chloride being greater than the volume of the predetermined dosage of said atropine.

* * * * *